(12) United States Patent
Ma

(10) Patent No.: US 6,497,902 B1
(45) Date of Patent: Dec. 24, 2002

(54) IONICALLY CROSSLINKED HYDROGELS WITH ADJUSTABLE GELATION TIME

(75) Inventor: Peter X. Ma, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/452,494

(22) Filed: Dec. 1, 1999

(51) Int. Cl.[7] .......................... A61K 9/14; A61K 31/74; A61K 33/06; A61K 33/10

(52) U.S. Cl. ................. 424/484; 424/78.12; 424/78.18; 424/682; 424/686; 424/687

(58) Field of Search .......................... 424/78.17, 78.18, 424/682, 686, 687, 484; 525/366

(56) References Cited

U.S. PATENT DOCUMENTS

| | | | |
|---|---|---|---|
| 3,455,701 A | * 7/1969 | Miller et al. ................. | 426/575 |
| 4,952,634 A | * 8/1990 | Grossman .................... | 525/366 |
| 5,308,701 A | * 5/1994 | Cohen et al. ................ | 525/366 |
| 6,150,581 A | * 11/2000 | Jiang et al. .................... | 602/50 |

OTHER PUBLICATIONS

C.K. Kuo and P. X. Ma, "Ionically crosslinked alginate hydrogels as scaffolds for tissue engineering", Proceedings of the 10th International Conference on Mechanics in Medicine and Biology, pp. 303–306 (1998).*
Chem. AG. 132:77740 Neiser, S. et al., 1999.*
Chem. Abstracts 114:26069, 1990.*
*Biomaterials science: an introduction to materials in medicine*, San Diego: Academic Press, edited by B. D. Ratner and A. S. Hoffman, Ch. 2.4: "Hydrogels", N. K. Peppas, 60–64 (1996).

L.J. Suggs, E.Y. Kao, L.L. Palombo, R.S. Krishnan, M.S. Widmer, and A.G. Mikos, "Preparation and characterization of poly(propylene fumarate–co–ethylene glycol) hydrogels". *J Biomater Sci Polym Edn*, 9(7): 653–666 (1998).
A. Atala, L. Cima, W.Kim, K. Paige, J. Vacanti, A. Retik, and C. Vacanti, "Injectable alginate seeded with chondrocytes as a potential treatment for vesicoureteral reflux", *J Urol*, 150(2 Pt 2): 745–747(1993).
C.K. Kuo and P.X. Ma, "Ionically crosslinked alignate hydrogels as scaffolds for tissue engineering", *Proceedings of the 10th International Conference on Mechanics in Medicine and Biology* 303–306 (1998).
P. Aebischer, E. Buchser, J. Joseph, J. Favre, N. deTribolet, M. Lysaght, S. Rudnick , and M. Goddard, "Transplantation in humans of encapsulated xenogeneic cells with immunosuppression: A preliminary report". *Transplantation*, 58(11): 1275–1277 (1994).

\* cited by examiner

*Primary Examiner*—Thurman K. Page
*Assistant Examiner*—Blessing Fubara
(74) *Attorney, Agent, or Firm*—Dierker & Glassmeyer, P.C.

(57) ABSTRACT

Biocompatible hydrogels, for: scaffoldings for tissue engineering; cell encapsulation matrices; injectable bulking materials for cosmetic and functional restorations; controlled release matrices; gene delivery vehicles; immunoprotection matrices; immobilization materials; food additives; medical gels; conductive electrode gels; lubricious coatings; film forming creams; membranes; superabsorbents; hydrophilic coatings; and wound dressings. The hydrogels include: at least one water-soluble polymer/copolymer; and at least one slow and/or fast dissolving and/or releasing divalent and/or multivalent cation-containing compound. At least one of the monomers is an acid, and/or contains an acid group or a derivative thereof. Such monomer reacts with the cations to form a three-dimensional ionically crosslinked hydrogel composition. A method for preparing such a composition comprises the step of controlling a rate of gel formation by varying at least one of: solubility of the cation containing compounds; cation concentration; mixture of cation containing compounds; polymer concentration; gelation temperature.

29 Claims, 3 Drawing Sheets

IONICALLY CROSSLINKED HYDROGELS WITH ADJUSTABLE GELATION TIME

BACKGROUND OF THE INVENTION

The invention relates in general to hydrogel compositions. More particularly, the present invention relates to ionically crosslinked hydrogels and a method for preparing and adjustably controlling the rate of gelation of the same.

Hydrogels are insoluble, hydrophilic water-containing gels, which are made from water-soluble polymers. See, for example, J. I. Kroschwitz, *Concise encyclopedia of polymer science and engineering,* New York: Wiley. xxix, 1341 (1990); and H. F. Mark and J. I. Kroschwitz, *Encyclopedia of polymer science and engineering,* 2nd ed. New York: Wiley. v. (1985). Hydrogels have received significant attention in the past three decades because of their high promise in biomedical applications. See, for example, N. A. Peppas, *Hydrogels in medicine and pharmacy,* Boca Raton, Fla.: CRC Press. (1986); and B. D. Ratner, *Biomaterials science: an introduction to materials in medicine,* San Diego: Academic Press. xi, 484 (1996). Their biocompatibility makes them widely used in the food industry, clinical medicine, pharmaceutical industry, and biomedical research. Food additives, contact lenses, blood contact materials, controlled release formulations, wound dressings, bioadhesives, membranes, superabsorbents, cell encapsulation and immunoisolation materials, and tissue engineering scaffolds are some of the examples. See, for example, P. Aebischer, E. Buchser, J. Joseph, J. Favre, N. de Tribolet, M. Lysaght, S. Rudnick, and M. Goddard, "Transplantation in humans of encapsulated xenogeneic cells without immunosuppression: A preliminary report". *Transplantation,* 58(11): 1275–1277 (1994); L. J. Suggs, E. Y. Kao, L. L. Palombo, R. S. Krishnan, M. S. Widmer, and A. G. Mikos, "Preparation and characterization of poly(propylene fumarate-co-ethylene glycol) hydrogels". *J Biomater Sci Polym Ed,* 9(7): 653–666 (1998); and A. Atala, L. Cima, W. Kim, K. Paige, J. Vacanti, A. Retik, and C. Vacanti, "Injectable alginate seeded with chondrocytes as a potential treatment for vesicoureteral reflux." *J Urol,* 150(2 Pt 2): 745–747 (1993).

In one prior attempt at making and using hydrogels, sodium alginate was dissolved in water. If cells, proteins or the like were to be included, they were then mixed into the alginate/water solution. The alginate solution was then dripped (via a syringe or the like) into a $CaCl_2$ solution. The outer surface of the alginate solution drop would immediately react with calcium ions to form a bead having a crosslinked outer surface. There are several drawbacks inherent in this procedure. First, the rendered structure is limited to beads having no uniformity, ie. there is no internal structure—the beads simply have a liquid interior with a hardened, crosslinked outer surface. This would lead to structurally non-homogeneous and mechanically weak alginate gels with undefined dimensions. Second, the rate of gelation is extremely fast and uncontrollable, which is undesirable in applications requiring slower and/or controllable gelation rates.

In other prior attempts at making and using hydrogels, harmful chemical crosslinking reagents were used. However, these reagents are toxic to cells and/or biosystems, and cannot be used for or with such cells and/or biosystems.

In yet another attempt at making and using hydrogels, alginate gels were proposed for use as impression material in dentistry. In this method, because alginates in and of themselves are so weak, about 50% ceramic powder is mixed with the alginate. Phosphate is then added as a retarder to the alginate/ceramic powder mixture in order to slow down the very fast reaction of the calcium ions with the alginate. The calcium ions from dissolved $CaCl_2$ react first with the phosphate, then the remaining calcium ions react with the alginate. However, drawbacks also exist in this method. Cells and the like cannot be incorporated into a gel including ceramic powder—cells and the like need a pure, clear gel in order to live and grow. Further, the use of phosphate as a reaction retarder greatly weakens the strength of the gel.

As can readily be appreciated, the need exists for, and it is an object of the present invention to provide structurally homogeneous and mechanically strong hydrogels having defined dimensions. It is another object of the present invention to provide such hydrogels wherein the rate of gelation is selectively variable and controllable.

SUMMARY OF THE INVENTION

The present invention addresses and solves the above-mentioned problems and meets the enumerated objects and advantages, as well as others not enumerated, by providing a biocompatible hydrogel composition, consisting essentially of:

at least one water-soluble polymer formed by polymerization of one or more monomers, the polymer being present in a predetermined concentration;

at least one of: a slow dissolving divalent or multivalent cation-containing compound; a slow releasing divalent or multivalent cation-releasing compound; a fast dissolving divalent or multivalent cation-containing compound; and a fast releasing divalent or multivalent cation-releasing compound, the at least one cation containing/releasing compound being present in a predetermined concentration;

wherein at least one of the monomers is selected from the group consisting of acids, monomers containing an acid group, monomers containing a derivative of an acid, and mixtures thereof, wherein the at least one monomer reacts with the divalent or multivalent cations to form ionic crosslinks intermolecularly among polymer chains to form an ionically crosslinked hydrogel composition at a gelation rate;

and wherein at least one of the concentration of the cation-containing/releasing compound and the concentration of the polymer substantially controls the gelation rate.

A method for preparing such an ionically crosslinked hydrogel composition comprises the step of controlling a rate of gel formation of the hydrogel composition by varying at least one of solubility of the cation containing compounds, cation concentration, mixture/ratio of cation containing compounds, polymer concentration, and gelation temperature.

BRIEF DESCRIPTION OF THE DRAWINGS

Other objects, features and advantages of the present invention will become apparent by reference to the following detailed description and drawings, in which.

DETAILED DESCRIPTION OF THE PREFERRED EMBODIMENTS

Figure 1:
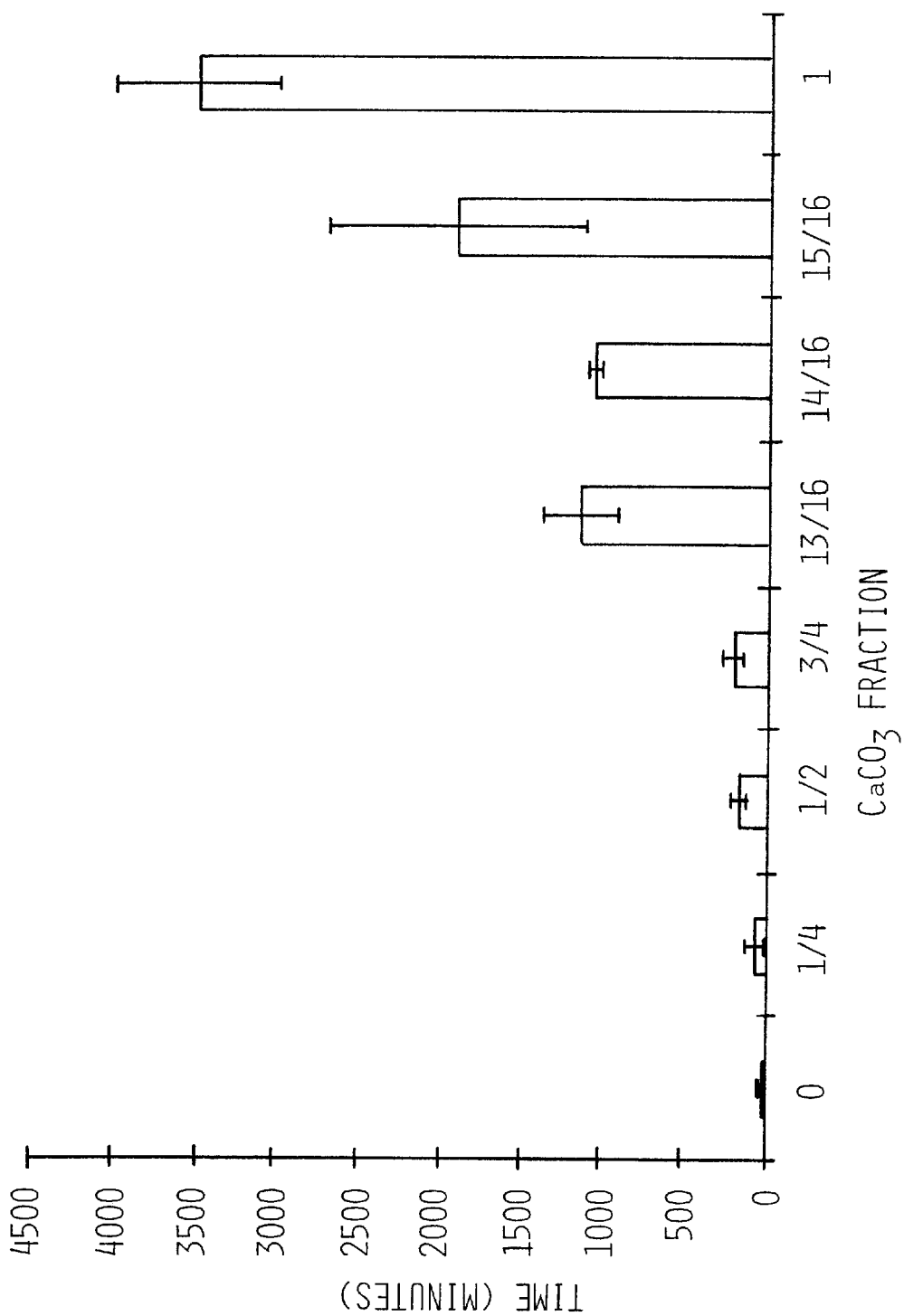
FIG. 1 is a graph (with standard deviation bars) showing gelation time of 1.5% LH alginate solution with varying $CaCO_3:CaSO_4$ molar ratios and a total calcium content of 1×.

The present invention provides novel ionically crosslinked hydrogel compositions having adjustably controllable gelation rates, such hydrogels fortuitously useful for a heretofore unexpectedly wide range of applications requiring varied gelation rates.

In aqueous solution, hydrogels may swell to an equilibrium volume but preserve their shape. The hydrophilicity is due to the presence of water-solubilizing groups, such as —OH, —COOH, —$CONH_2$, —CONH—, —$SO_3H$, etc. It is believed that the stability of shape is due to the presence of the present inventive three-dimensional network, which is maintained by crosslinks between polymer chains. These crosslinks can be covalent bonds, ionic bonds, hydrogen bonds, hydrophobic associations, and dipole-dipole interactions.

The inventive ionically crosslinked hydrogels may be very attractive candidates for biomedical applications because of their exceptional biocompatibility without the involvement of harmful chemical crosslinking reagents. For many of these applications, the structural uniformity, mechanical stability, and controllable gelation time are of essential importance. Considerable success, as disclosed further hereinbelow, has been achieved in controlling the structural uniformity and mechanical stability of ionically crosslinked hydrogels in an aqueous environment. See, for example, C. K. Kuo and P. X. Ma, "Ionically crosslinked alginate hydrogels as scaffolds for tissue engineering," *Proceedings of the 10th International Conference on Mechanics in Medicine and Biology*: 303–306 (Mar. 2–5, 1998), which is incorporated herein by reference in its entirety.

The present invention contemplates a method for tissue engineering in vitro comprising the steps of: a) providing: i) cells, ii) an alginate salt, iii) a source of calcium ions, and iv) a calcium releasing compound; b) mixing the cells, alginate salt, and the source of calcium ions to provide a mixture; c) adding the calcium releasing compound to the mixture to provide a crosslinked gel; and d) culturing the crosslinked gel to provide a three-dimensional crosslinked hydrogel/cell system for growing cells in vitro.

In one embodiment, the alginate salt is selected from the group consisting of sodium alginate and potassium alginate. In another embodiment, the alginate salt is prepared from an alginate source selected from *Macrocystis pyrifera* and *Laminaria hyperborea*. In yet another embodiment, the source of calcium ions is selected from the group consisting of calcium carbonate and calcium sulfate. In an alternative embodiment, the calcium releasing compound is D-glucono-δ-lactone.

In another embodiment, the method further comprises the step of implanting the three-dimensional crosslinked hydrogel/cell system. In one embodiment, the three-dimensional crosslinked hydrogel/cell system has a thickness of between about 4 mm and about 8 mm, and a diameter of approximately 18 mm.

It is not intended that the present invention be limited for culturing a particular type of cells (or merely one cell type on a scaffold). A variety of cell types (including mixtures of different cells) are contemplated. In one embodiment, the cells are osteoblasts. In another embodiment, the cells secrete a medically useful compound (eg., hormone, cytokine, etc.). Such cells may be (but need not be) cells that have been manipulated by recombinant means to secrete such compounds.

The present invention also contemplates the resulting crosslinked alginate gel as a composition. Moreover, the present invention contemplates the resulting crosslinked gel in combination with other components, such as cells. It is not intended that the cells be limited to particular cell type, or merely one cell type on a scaffold. A variety of cell types, including mixtures of different cells, are contemplated.

As used herein, the term "alginate" refers to any of several derivatives of alginic acid (eg., calcium, sodium, or potassium salts or propylene glycol alginate). These compounds are hydrophilic colloids obtained from seaweed.

The methods of the present invention permit the formation and preparation of structurally homogeneous and mechanically strong alginate gels with defined dimensions, which can be used to incorporate living cells. The three dimensional gel structure with incorporated cells can be maintained in an in vitro tissue culture environment by adjusting calcium ion concentration in the culture medium. Ionically crosslinked alginate gels with defined three dimensional structure can be reliably used as a tissue engineering scaffold.

In addition to the advantages stated immediately hereinabove, it would further be advantageous to control the gelation rate of hydrogels, in that for many applications such as in biomedical, pharmaceutical, food and cosmetic formulations, the gelation rate may be critical. For some applications, a slower gelation rate is preferred (hours to days); whereas for others, a faster gelation rate is preferred (instant, or seconds to minutes); whereas for still others, an intermediate gelation rate is preferred (minutes to hours).

For example, the gel-forming solution or paste (alone or with other ingredients) can be used as an injectable material to cast into a three-dimensional shape with structural uniformity and superior mechanical properties. A slower gelation rate is preferred because it can result in uniform gel formation and better mechanical properties. For another application, such as filling materials to block a leakage in a blood vessel or intestines, a fast gelation rate may be essential to ensure a gel formation before being diluted or flushed away. In another example, the gels can be used as filling materials (with cells or not, with biological agents or not) to repair a complex tissue/organ defect(s) in situ by a reconstructive/plastic surgeon. The surgeon needs enough working time to shape the material before it gels (forms three-dimensional structures). However, the gelation time should also be reasonably short so that the structure "solidifies" after the shaping procedure without prolonged patient waiting and shape-maintaining time.

As such, it can be seen that, for a particular end-use for hydrogels, the necessary/preferred rate of gelation falls within relatively narrow parameters. Thus, for the hydrogels to be useful, their gelation rate should fall within such parameter(s). To be far more useful, the gelation rate of the hydrogels should be controllable so as to fall within such parameter(s) for a wide range of particular end-uses (which end-uses prefer rates of gelation ranging from fast to slow). The present invention, in meeting this need, is based upon the unexpected and fortuitous discovery that the gelation rate of ionically crosslinked hydrogels may be selectively varied and controlled to advantageously meet a wide range of relatively narrow end-use parameter(s) (eg. rates of gelation).

The present invention provides ionically crosslinked hydrogels with controlled gelation time. Both the exemplary compositions and the methods of preparing such hydrogels are disclosed. The hydrogels are made of one or more synthetic and/or natural water-soluble polymers (macromolecules), and one or more divalent or multivalent cation containing or releasing compounds. The polymers can be either homopolymers or copolymers (with two or more types of structural units). The copolymers can be random copolymers, block copolymers, or graft copolymers. At least one of the structural units (monomers) is an acid (e.g., carboxylic acid, sulfonic acid and phosphonic acid), or contains an acid group or a derivative of an acid (such as its salt, ester, or anhydride) that can react with divalent and/or multivalent cations to form ionic crosslinks intermolecularly among polymer chains. A cation containing compound can either directly dissolve in an aqueous solution to produce free cations or react with one or more other reactants to release the cations. Such reactants are defined herein as "cation releasing compounds."

The cation releasing compound need simply cause the cation source to release cations, thereby initiating gelation. It is to be understood that any suitable cation releasing compound may be used in conjunction with the present invention. In one embodiment, the cation releasing compound comprises D-glucono-δ-lactone ($C_6H_{10}O_6$) (GDL), and causes release of calcium cations. Without being bound to any theory, it is believed that the GDL functions in the following manner. The GDL slowly hydrolyzes into an acid, thereby lowering the pH in its vicinity. This causes the $CaCO_3$ to dissolve (which is generally insoluble in a neutral solution), presumably due to the now-mildly acidic solution. As such, it is believed that the GDL may be useful to cause release of cations from any cation containing compound which is generally insoluble in a neutral solution.

Further, in lieu of the GDL, after a generally insoluble cation containing compound is suspended with the water soluble polymer, it is within the purview of the present invention to slowly add an acid to the suspension in order to lower the pH and cause release of the cation.

The inventor of the present methods of preparing an ionically crosslinked gel has unexpectedly found that utilizing one or more of: the solubility of the cation containing compounds; cation concentration; mixture/ratio of cation containing compounds; polymer concentration; gelation temperature; and so forth controls the rate of gel formation.

The divalent or multivalent cation(s) contained or released from the source compounds are selected from the group consisting of calcium, magnesium, beryllium, strontium, barium, radium, aluminum, copper, zinc, osmium or any other divalent or multivalent cations that can form ionic bonds with the acid(s) or its derivatives contained in the water-soluble polymers, and mixtures thereof.

A few examples of published reference materials to which a skilled artisan may look to determine if a cation containing/releasing compound would be a fast or slow dissolving/releasing compound include, but are not limited to the "Solubility Product Constants" table from the *CRC Handbook of Chemistry and Physics*, available, for example, from Knovel Engineering & Scientific Online References at www.knovel.com; the "Aqueous Solubility of Inorganic Compounds at Various Temperatures" table, also from the *CRC Handbook of Chemistry and Physics;* and *The Merck Index, An Encyclopedia of Chemicals, Drugs, and Biologicals,* Budavari, O'Neil and Smith, Editors, 11th Edition, published by Merck & Co., Inc. (1989).

Some exemplary suitable acid-containing monomers that may constitute the polymers include but are not limited to the following: 1) Monomers containing carboxyl: D-glucopyramuronic acid, D-manopyranuronic acid, D-galactopyranuronic acid, 4-O-methyl-D-glycopyranuronic acid, L-idopyranuronic acid, L-idopyranuronic acid, L-gulopyranuronic acid, sialic acids, acrylic acid, methacrylic acid, 4-vinylbenzoic acid, crotonic acid, oleic acid, elaidic acid, itaconic acid, maleic acid, fumaric acid, acetylenedicarboxylic acid, tricarbollylic acid, sorbic acid, linoleic acid, linolenic acid, eicosapentenoic acid, other unsaturated carboxylic acids, and their derivatives such as salts, anhydrides, and esters; 2) Monomers with other acids such as sulfonic acid, or phosphonic acid replacement of the carboxyl group of the above listed monomers and their derivatives.

It is to be understood that any polymers that are made from one or more of the above monomers with or without other monomers may be suitable to form hydrogels according to the present invention. Some exemplary other monomers (not the acid or acid derivative containing monomers) include but are not limited to the following: D-xylopyranose, L-arabinopyranose, L-arabinofuranose, D-glucopyranose, D-mannopyranose, D-galactopyranose, L-galactopyranose, D-fructofuranose, D-galactofuranose D-glucosamine, D-galactosamine, methacrylates (e.g., methyl methacrylate), ethylene, propylene, tetrafluoroethylene, styrene, vinyl chloride, vinylidene chloride, vinyl acetate, acrylonitrile, 2,2-bis[4-(2-hydroxy-3-methacryloyloxy-propyloxy)-phenyl]propane(BisGMA), ethyleneglycol dimethacrylate (EGDMA), triethyleneglycol dimethacrylate (TEGDMA), bis(2-methacrylyoxyethyl) ester of isophthalic acid (MEI), bis(2-methacrylyoxyethyl) ester of terephthalic acid (MET), bis(2-methacrylyoxyethyl) ester of phthalic acid (MEP), 2,2-bis-(4-methacrylyoxy phenyl)propane(BisMA), 2,2-bis[4-(2-methacrylyloxyethoxy)phenyl]propane (BisEMA), 2,2,-bis[4-(3-methacrylyloxypropoxy)phenyl]propane (BisPMA), hexafluoro-1,5-pentanediol dimethacrylate (HFPDMA), bis-(2-methacrylyloxyethoxyhexafluoro-2-propyl)benzene [Bis(MEHFP)φ], 1,6-bis(methacrylyloxy-2-ethoxycarbonylamino)-2,4,4-trimethylhexan (UEDMA), spiro orthocarbonates, and the derivatives of these monomers.

An exemplary list of some polymers that can be made into ionically crosslinked hydrogels with controlled gelation time includes but is not limited to the following: alginic acid, pectin, hyaluronic acid, heparin, proteins, proteoglycans, poly(methacrylic acid), poly(acrylic acid), poly(maleic anhydride), poly(maleic acid), poly(methyl methacrylate-methacrylic acid), poly(methyl acrylate-acrylic acid), poly(methyl methacrylate-acrylic acid), poly(ethyl acrylate-acrylic acid), poly(ethyl methacrylate-methacrylic acid), poly(butyl acrylate-acrylic acid), poly(ethylene-acrylic acid), poly(ethylene-methacrylic acid), poly(acrylonitrile-maleic anhydride), poly(butadiene-acrylonitrile-acrylic acid), poly(butadiene-maleic acid), poly(butadiene-maleic anhydride), poly(acrylamide-acrylic acid), poly(2-hydroxyethyl methacrylate-methacrylic acid), poly(propylene-acrylic acid), poly(propylene-ethyleneacrylic acid), poly(vinyl chloride-vinyl acetate-maleic acid), and derivatives of the polymers (salts, anhydrides, esters, etc.).

It is also to be understood that the above listed polymers can be used together with other polymers, including but not limited to water soluble polymers such as gelatin, agar, agarose, chitin/chitosan, cellulose, collagen, poly(vinyl alcohol), poly(ethylene oxide), Pluronics (block copolymers of ethylene oxide and propylene oxide), poly(2-hydroxyethyl methacrylate), and poly(N-vinylpyrrolidinone).

It is to be understood that this invention is conceptually suitable for all the aforementioned polymer systems, and as such, the supporting experimental data hereinbelow are not intended to be exhaustive. Instead, they are collected primarily from alginates as representative ionically crosslinked hydrogels.

These hydrogels might be used in a variety of biomedical, pharmaceutical, food, cosmetic and other applications. They could be used as scaffoldings for tissue engineering, cell encapsulation matrices, injectable bulking materials for cosmetic and functional restorations, controlled release matrices, gene delivery vehicles, immunoprotection matrices, immobilization materials, food additives, medical gels, conductive electrode gels, lubricious coatings, film forming creams, membranes, superabsorbents, hydrophilic coatings, wound dressings, and so forth. It is to be understood that the term "biocompatible hydrogel" as used herein is intended to include, but not be limited to all of the uses enumerated immediately hereinabove, as well as throughout the present disclosure.

It is further contemplated as being within the purview of the present invention to include other minor components in the ionically crosslinked hydrogels of the present invention. For example, inert components and bioactive agents (such as, for example, growth factors and hormones) may be incorporated thereinto if desired, without substantially affecting the methods and/or compositions of the present invention.

Although alginates from various sources such as *Laminaria hyperborea, Laminaria digitata, Eclonia maxima, Macrocystis pyrifera, Lessonia nigrescens, Ascophyllum codosum, Laminaria japonica, Durvillaea antarctica,* and *Durvillaea potatorum* in a variety of salt forms can be used, two sodium alginates from *Laminaria hyperborea* (LH) and *Macrocystis pyrifera* (MP) are used in the exemplary preferred embodiments.

It is to be understood that various cations from countless compounds can potentially be used as ionic crosslinkers. However, in the preferred embodiments, calcium ions from calcium carbonate ($CaCO_3$) and calcium sulfate dihydrate ($CaSO_4.2H_2O$) are used in the exemplary embodiments as representative slow dissolving and fast dissolving calcium containing compounds, respectively. For example, water soluble $CaCl_2$ or other cation containing compounds can be used instead of $CaSO_4.2H_2O$. Although calcium sulfate may be used, the calcium sulfate dihydrate is preferred in that the dihydrate is its naturally occurring form, and is water soluble.

It is to be understood that the calcium ion to carboxyl molar ratio of the present invention may range between about 0.05 and about 2.0, and the ratio of $CaCO_3$ to $CaSO_4.2H_2O$ may range between about 98:2 and about 2:98. In a preferred embodiment, the calcium ion to carboxyl molar ratio of the present invention may range between about 0.18 and about 0.9, and the ratio of $CaCO_3$ to $CaSO_4.2H_2O$ may range between about 90:10 and about 50:50. In a more preferred embodiment, the calcium ion to carboxyl molar ratio of the present invention may range between about 0.27 and about 0.54, and the ratio of $CaCO_3$ to $CaSO_4.2H_2O$ may range between about 65:35 and about 85:15.

It is to be understood that various aqueous solutions can be used to make the hydrogels (water, saline solution, buffer solutions, tissue culture mediums, etc.). However, in the preferred embodiments, water is used.

Sodium alginate prepared from *Laminaria hyperborea* (LH) is commercially available under the trade name PROTANAL LF200 from Pronova Biopolymer in Drammen, Norway. High viscosity sodium alginate prepared from *Macrocystis pyrifera* (MP), calcium carbonate ($CaCO_3$), calcium chloride dihydrate ($CaCl_2.2H_2O$), calcium sulfate dihydrate ($CaSO_4.2H_2O$), and D-glucono-delta-lactone ($C_6H_{10}O_6$) (GDL) are commercially available from Sigma Chemical Company in St. Louis, Mo.

To further illustrate the process and composition of the present invention, the following examples are given. It is to be understood that these examples are provided for illustrative purposes and are not to be construed as limiting the scope of the present invention.

EXAMPLE I

Sodium alginate was dissolved in deionized water. Calcium sulfate dihydrate ($CaSO_4.2H_2O$) alone, calcium carbonate ($CaCO_3$) in combination with GDL, or $CaCO_3$-GDL mixed with $CaSO_4$ were used as sources of calcium ions to initiate gelation. The indicated alginate gel concentrations in this disclosure were the final weight/volume concentrations. When $CaCO_3$ was used, a $CaCO_3$ to GDL molar ratio of 0.5 was generally maintained in the exemplary embodiments of the invention to achieve a neutral pH value. However, this does not mean the invention is limited to this molar ratio. For the alginate gels, a basic calcium ion to carboxyl molar ratio of 0.18 was designated as 1×. The crosslinking density was adjusted with a multiplication factor to this molar ratio as a relative calcium ion content, such as 0.5×(molar ratio: 0.09), 1.5×(molar ratio: 0.27), 2×(molar ratio: 0.36), and so forth.

Figure 4:
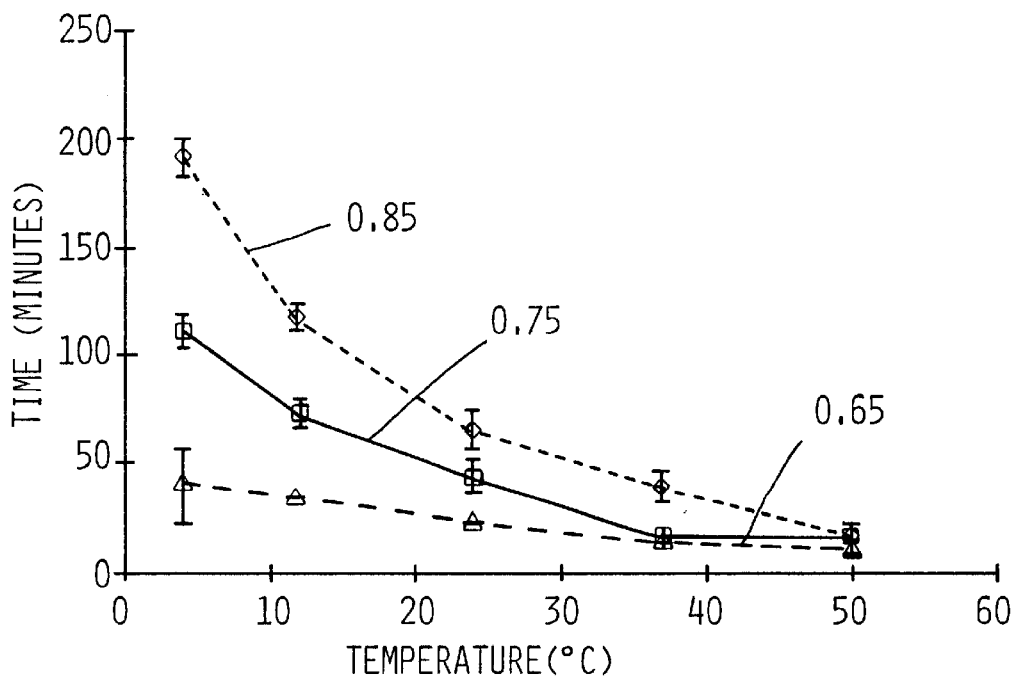
FIG. 4 is a graph (with standard deviation bars) showing gelation time as a function of temperature for 1.5% LH alginate solution with a total calcium content of 2×($CaCO_3$:$CaSO_4 \cdot 2H_2O$=65:35, 75:25, and 85:15)

The amount of time required for gelation was obtained by detection of flow by the naked eye. When $CaCO_3$ alone was used as the source of calcium ions, sodium alginate solution was added to a $CaCO_3$ suspension in water, mixed and vortexed for one minute. A fresh aqueous GDL solution was then added to the suspension and vortexed for 20 seconds to initiate gelation. When calcium sulfate alone was used as a source of calcium ions, calcium sulfate dihydrate ($CaSO_4.2H_2O$) was dispersed in deionized (dI) water. The suspension was added to sodium alginate solution and vortexed for 20 seconds. Gels in which both $CaCO_3$ and $CaSO_4.2H_2O$ provided crosslinking calcium ions were made so that the total molar concentration of calcium added up to a specific calcium content. Sodium alginate solution was equilibrated for at least 3 hours to a desired temperature (temperatures as shown in FIG. 4) before initiating gelation. The sodium alginate solution was added to the $CaCO_3$ suspension in dI $H_2O$, mixed and vortexed for one minute, and transferred into vials. The suspensions were allowed to equilibrate to the desired gelation temperature for 45 minutes. A fresh aqueous GDL solution was then transferred to $CaSO_4.2H_2O$ to form a suspension that was added to each sample. The final suspension was vortexed for 20 seconds and immediately returned to the specific temperature for gelation to occur. The averages and the standard deviations of triplets were reported.

Discussion of Experimental Results

Effects of Calcium Source. $CaSO_4.2H_2O$ reacted with the polymer too quickly to form uniform gels. The gels formed consisted of lumps of varying density. The reaction rate of MP alginate with $CaSO_4.2H_2O$ was slightly slower than that of LH alginate. The $CaCO_3$-GDL system provides a slower gelation process that forms gels with uniform structures.

Figure 2:
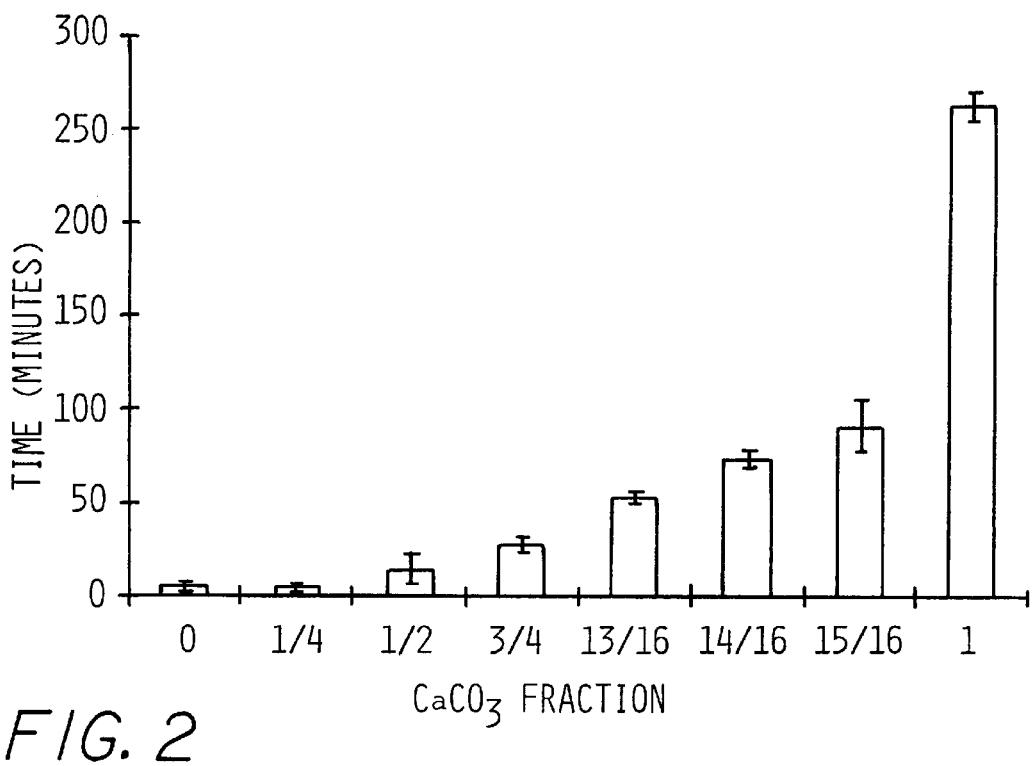
FIG. 2 is a graph (with standard deviation bars) showing gelation time of 1.5% LH alginate solution with varying $CaCO_3:CaSO_4$ molar ratios and a total calcium content of 2×.
Figure 3:
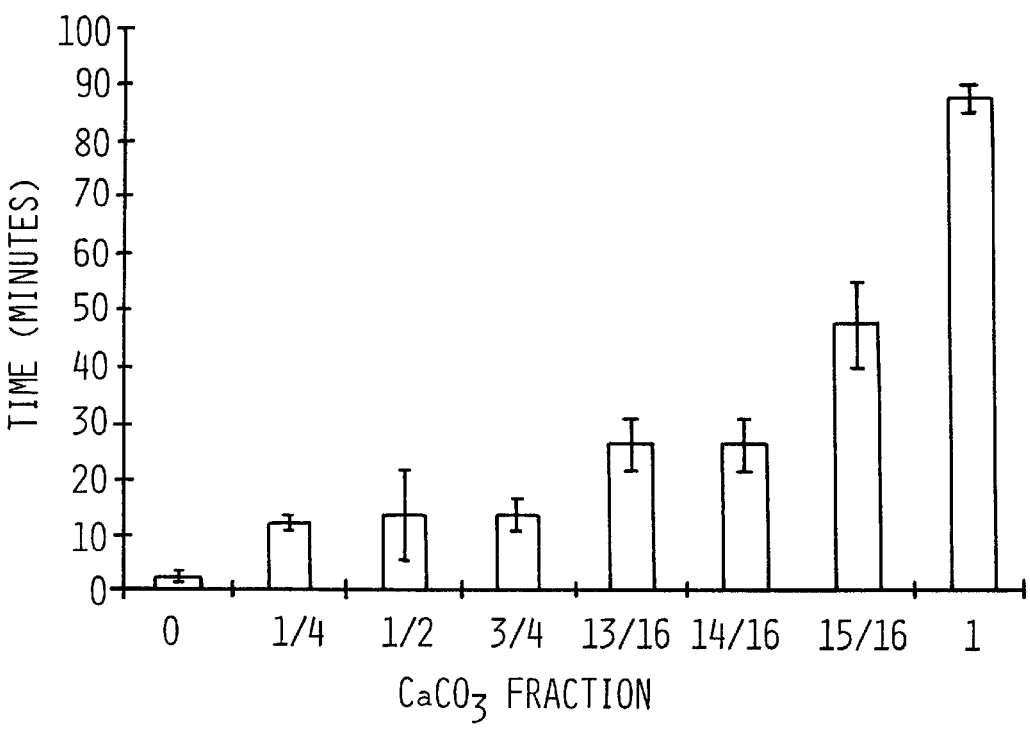
FIG. 3 is a graph (with standard deviation bars) showing gelation time of 1.5% LH alginate solution with varying $CaCO_3$:$CaSO_4$ molar ratios and a total calcium content of 3×.

Gelation time profiles for 1.5% LH alginate gels with 1×, 2×, and 3×Ca were obtained for varying ratios of $CaCO_3:CaSO_4.2H_2O$. Gelation time decreased with increasing $CaSO_4$ content (FIGS. 1–3).

Effects of Crosslinking Density. For all the formulations with the same $CaCO_3:CaSO_4.2H_2O$ ratio, the gelation time decreased with calcium content (comparing FIGS. 1 through 3).

Effects of Temperature. Gelation time was also characterized as a function of temperature. Gels of 1.5% LH alginate with 2×Ca ($CaCO_3:CaSO_4.2H_2O$=65:35, 75:25, 85:15) were made at a few different temperatures between 4° C. and 50° C. The gelation time decreased with increasing temperature (FIG. 4). $CaSO_4.2H_2O$ may have a higher solubility at a high temperature, contributing to a higher gelation rate. GDL probably hydrolyzed more rapidly at the higher temperature, resulting in a faster release of calcium ions from $CaCO_3$ into the sodium alginate solution, leading to a higher gelation rate. The solubility of $CaCO_3$ in water may also increase at a higher temperature, leading to a higher gelation rate.

Figure 5:
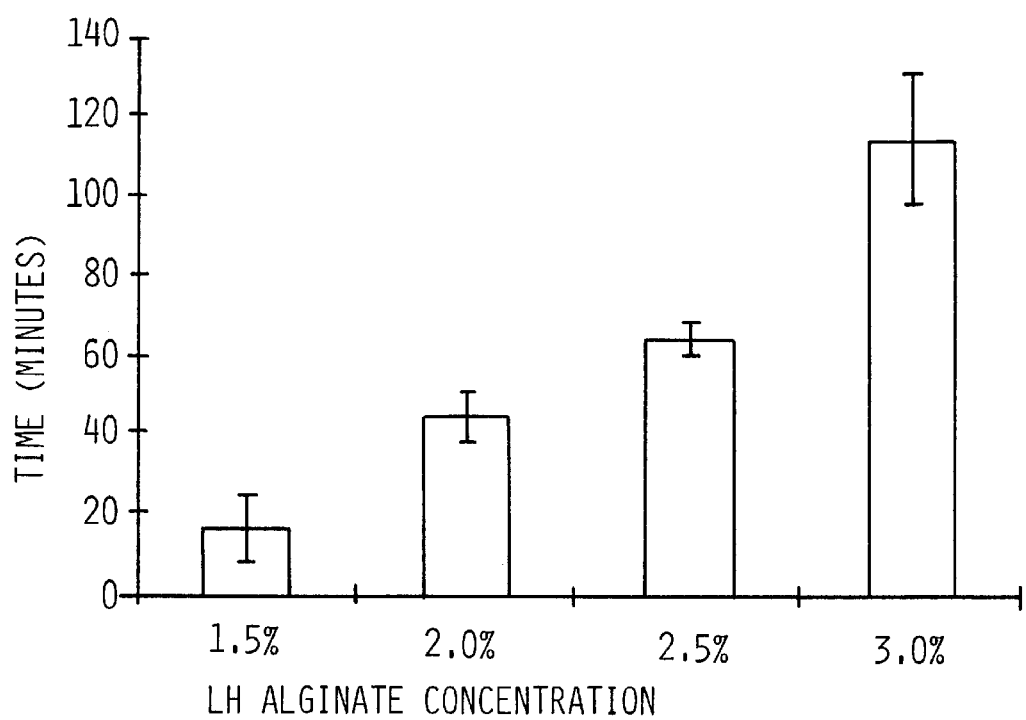
FIG. 5 is a graph (with standard deviation bars) showing gelation time vs. LH alginate concentration with a total calcium content of 2×($CaCO_3$:$CaSO_4 \cdot 2H_2O$=50:50).

Effects of Polymer Concentration. Gels of 2×Ca ($CaCO_3:CaSO_4.2H_2O$=50:50) were made to study the effect of polymer concentration. The gels exhibited increasing gelation time with polymer concentration in the concentration range studied (FIG. 5).

EXAMPLE II

Hyaluronic acid, sodium hyaluronate, or potassium hyaluronate is dissolved in water (dI water, buffered aqueous solution, or tissue culture medium). A $CaCO_3$ suspension in water is added into the solution and mixed. A fresh aqueous GDL solution is then added to the suspension and vortexed to initiate slow gelation. Calcium sulfate alone, ie. without $CaCO_3$, can be used as a source of calcium ions for fast gelation. Calcium sulfate dihydrate is dispersed in water. The suspension is added to the hyaluronic acid solution and vortexed. Gels in which both $CaCO_3$ and $CaSO_4.2H_2O$ provide crosslinking calcium ions can also be made to have an intermediate gelation rate. The hyaluronic acid solution is equilibrated for about 3 hours at a desired temperature ranging between about 4° C. and about 50° C. and is then added to the $CaCO_3$ suspension in $H_2O$, mixed and vortexed for about 1 minute, and transferred into a container or mold. A fresh aqueous GDL solution is then transferred to $CaSO_4.2H_2O$ to form a suspension that is then added to the hyaluronic acid/$CaCO_3$ suspension. The final suspension is vortexed for about 20 seconds and immediately returned to the specific temperature for gelation to occur. Any or a combination of: solubility of the calcium containing compounds; different calcium concentrations; the ratios of $CaCO_3:CaSO_4.2H_2O$; hyaluronic acid concentrations; and gelation temperatures are expected to result in selectively different and controllable gelation rates of ionically crosslinked hyaluronate gels. These gels can be used for similar applications to those for alginate gels.

EXAMPLE III

Poly(acrylic acid), or its sodium or potassium salt, is dissolved in water (dI water, buffered aqueous solution, or tissue culture medium). A $CaCO_3$ suspension in water is added into the solution and mixed. A fresh aqueous GDL solution is then added to the suspension and vortexed to initiate slow gelation. Calcium sulfate alone, ie. without $CaCO_3$, can be used as a source of calcium ions for fast gelation. Calcium sulfate dihydrate is dispersed in water. The suspension is added to the poly(acrylic acid) solution and vortexed. Gels in which both $CaCO_3$ and $CaSO_4.2H_2O$ provide crosslinking calcium ions can also be made to have an intermediate gelation rate. The poly(acrylic acid) solution is equilibrated for about 3 hours at a desired temperature ranging between about 4° C. and about 50° C. and is then added to the $CaCO_3$ suspension in $H_2O$, mixed and vortexed for about 1 minute, and transferred into a container or mold. A fresh aqueous GDL solution is then transferred to $CaSO_4.2H_2O$ to form a suspension that is then added to the poly(acrylic acid)/$CaCO_3$ suspension. The final suspension is vortexed for about 20 seconds and immediately returned to the specific temperature for gelation to occur. Any or a combination of: solubility of the calcium containing compounds; different calcium concentrations; the ratios of $CaCO_3:CaSO_4.2H_2O$; poly(acrylic acid) concentrations; and gelation temperatures are expected to result in selectively different and controllable gelation rates of ionically crosslinked polyacrylate gels. These gels may find use as, for example, glues (for dental work or the like, or for any other conventional adhesive uses).

While the present invention is particularly drawn to hydrogels for use with biological systems, it is to be understood that it is within the purview of the present invention that the inventive hydrogels may be useful for a wide range of non-biological systems.

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A hydrogel composition, comprising:
   at least one water-soluble polymer composed of one or more monomers, the polymer being present in a predetermined concentration;
   at least one of: a first divalent or multivalent cation-containing compound having a $K_{sp}$ at or less than $3.36 \times 10^{-9}$; and a first divalent or multivalent cation-releasing compound, the at least one first divalent or multivalent cation-containing compound and the first divalent or multivalent cation-releasing compound being present in a predetermined concentration; and
   at least one of a second divalent or multivalent cation-containing compound having a $K_{sp}$ at or greater than $3.14 \times 10^{-5}$; and a second divalent or multivalent cation-releasing compound, the at least one second divalent or multivalent cation-containing compound and the second divalent or multivalent cation-releasing compound being present in a predetermined concentration, wherein the $K_{sp}$ of the second cation-containing compound is greater than the $K_{sp}$ of the first cation-containing compound;
   wherein at least one of the monomers is selected from the group consisting of acids, monomers containing an acid group, monomers containing a derivative of an acid, and mixtures thereof, wherein the at least one monomer reacts with the divalent or multivalent cations to form ionic cross-links inter-molecularly among polymer chains to form an ionically cross-linked hydrogel composition;

and wherein the first and second divalent or multivalent cations are selected from the group consisting of calcium, beryllium, strontium, barium, radium, aluminum, copper, zinc, osmium, and mixtures thereof.

2. The hydrogel composition as defined in claim 1 wherein the water-soluble polymer is at least one of a synthetic polymer and a natural polymer.

3. The hydrogel composition as defined in claim 1 wherein the polymer is selected from the group consisting of homopolymers, copolymers, random copolymers, block copolymers, graft copolymers, and mixtures thereof.

4. The hydrogel composition as defined in claim 1 wherein the monomers containing an acid group are monomers containing a carboxyl group selected from the group consisting of D-glucopyramuronic acid, D-manopyranuronic acid, D-galactopyranuronic acid, 4-O-methyl-D-glycopyranuronic acid, L-idopyranuronic acid, L-idopyranuronic acid, L-gulopyranuronic acid, sialic acids, acrylic acid, methacrylic acid, 4-vinylbenzoic acid, crotonic acid, oleic acid, elaidic acid, itaconic acid, maleic acid, fumaric acid, acetylenedicarboxylic acid, tricarbollylic acid, sorbic acid, linoleic acid, linolenic acid, eicosapentenoic acid, unsaturated carboxylic acids, derivatives thereof, and mixtures thereof.

5. The hydrogel composition as defined in claim 4 wherein the carboxyl group of the monomers is replaced by the group consisting of sulfonic acid, phosphonic acid, derivatives thereof, and mixtures thereof.

6. The hydrogel composition as defined in claim 1 wherein the acids are selected from the group consisting of carboxylic acid, sulfonic acid, phosphoric acid, and mixtures thereof.

7. The hydrogel composition as defined in claim 1 wherein the polymer is selected from the group consisting of alginic acid, pectin, hyaluronic acid, heparin, proteins, proteoglycans, poly(methacrylic acid), poly(acrylic acid), poly(maleic anhydride), poly(maleic acid), poly(methyl methacrylate-methacrylic acid), poly(methyl acrylate-acrylic acid), poly(methyl methacrylate-acrylic acid), poly(ethyl acrylate-acrylic acid), poly(ethyl methacrylate-methacrylic acid), poly(butyl acrylate-acrylic acid), poly(ethylene-acrylic acid), poly(ethylene-methacrylic acid), poly(acrylo-nitrile-maleic anhydride), poly(butadiene-acrylonitrile-acrylic acid), poly(butadiene-maleic acid), poly(butadiene-maleic anhydride), poly(acrylamide-acrylic acid), poly(2-hydroxyethyl methacrylate-methacrylic acid), poly(propylene-acrylic acid), poly(propylene-ethylene-acrylic acid), poly(vinyl chloride-vinyl acetate-maleic acid), derivatives thereof, and mixtures thereof.

8. The hydrogel composition as defined in claim 1 wherein the hydrogel composition contains a predetermined ratio of the at least one first cation-containing compound and the first divalent or multivalent cation-releasing compound to the at least one second cation-containing compound and the second divalent or multivalent cation-releasing compound, wherein the predetermined ratio substantially controls the gelation rate.

9. The hydrogel composition as defined in claim 8 wherein the polymer is selected from the group consisting of sodium alginate, potassium alginate, and mixtures thereof, the second divalent or multivalent cation-containing compound is calcium sulfate dihydrate ($CaSO_4 \cdot 2H_2O$), the first divalent or multivalent cation-containing compound is calcium carbonate ($CaCO_3$), and wherein the composition further consists essentially of D-glucono-delta-lactone (GDL).

10. The hydrogel composition as defined in claim 9 wherein the calcium ion to carboxyl molar ratio ranges between about 0.05 and about 2.0, and wherein the ratio of $CaCO_3$ to $CaSO_4 \cdot 2H_2O$ ranges between about 98:2 and about 2:98.

11. The hydrogel composition as defined in claim 9 wherein the calcium ion to carboxyl molar ratio ranges between about 0.27 and about 0.54, and wherein the ratio of $CaCO_3$ to $CaSO_4 \cdot 2H_2O$ ranges between about 65:35 and about 85:15.

12. A biocompatible hydrogel composition, comprising:

at least one water-soluble polymer composed of one or more monomers, the polymer being present in a predetermined concentration;

at least one of: a first divalent or multivalent cation-containing compound having a $K_{sp}$ at or less than $3.36 \times 10^{-9}$; and a first divalent or multivalent cation-releasing compound, the at least one first divalent or multivalent cation-containing compound and the first divalent or multivalent cation-releasing compound being present in a predetermined concentration; and at least one of: a second divalent or multivalent cation-containing compound having a $K_{sp}$ at or greater than $3.14 \times 10^{-5}$; and a second divalent or multivalent cation-releasing compound, the at least one second divalent or multivalent cation-containing compound and the second divalent or multivalent cation-releasing compound being present in a predetermined concentration, wherein the $K_{sp}$ of the second cation-containing compound is greater than the $K_{sp}$ of the first cation-containing compound;

wherein at least one of the monomers is selected from the group consisting of acids, monomers containing an acid group, monomers containing a derivative of an acid, and mixtures thereof, wherein the at least one monomer reacts with the divalent or multivalent cations to form ionic cross-links inter-molecularly among polymer chains to form an ionically cross-linked hydrogel composition at a gelation rate;

wherein the hydrogel composition contains a predetermined ratio of the at least one first divalent or multivalent cation-containing compound and the first divalent or multivalent cation-releasing compound to the at least one second divalent or multivalent cation-containing compound and the second divalent or multivalent cation-releasing compound, wherein at least one of: the predetermined ratio; the first divalent or multivalent cation-containing/divalent or multivalent cation-releasing compound concentration; the second divalent or multivalent cation-containing/divalent or multivalent cation-releasing compound concentration; and the polymer concentration substantially controls the gelation rate;

and wherein the first and second divalent or multivalent cations are selected from the group consisting of calcium, beryllium, strontium, barium, radium, aluminum, copper, zinc, osmium, and mixtures thereof.

13. The biocompatible hydrogel composition as defined in claim 12 wherein the polymer is selected from the group consisting of sodium alginate, potassium alginate, and mixtures thereof, the second divalent or multivalent cation-containing compound is calcium sulfate dihydrate ($CaSO_4 \cdot 2H_2O$), the first divalent or multivalent cation-containing compound is calcium carbonate ($CaCO_3$), and wherein the composition further consists essentially of D-glucono-delta-lactone (GDL).

14. The biocompatible hydrogel composition as defined in claim 13 wherein the calcium ion to carboxyl molar ratio ranges between about 0.05 and about 2.0, and wherein the ratio of $CaCO_3$ to $CaSO_4.2H_2O$ ranges between about 98:2 and about 2:98.

15. The biocompatible hydrogel composition as defined in claim 14 wherein the calcium ion to carboxyl molar ratio ranges between about 0.27 and about 0.54, and wherein the ratio of $CaCO_3$ to $CaSO_4.2H_2O$ ranges between about 65:35 and about 85:15.

16. A method for preparing an ionically cross-linked hydrogel composition, the method comprising the step of:
selectively controlling a rate of gel formation of the hydrogel composition which comprises: at least one water-soluble polymer composed of one or more monomers, the polymer being present in a predetermined concentration; at least one of: a first divalent or multivalent cation-containing compound having a $K_{sp}$ at or less than $3.36\times10^{-9}$; and a first divalent or multivalent cation-releasing compound, the at least one first divalent or multivalent cation-containing compound and the first divalent or multivalent cation-releasing compound being present in a predetermined concentration; and at least one of: a second divalent or multivalent cation-containing compound having a $K_{sp}$ at or greater than $3.14\times10^{-5}$; and a second divalent or multivalent cation-releasing compound, the at least one second divalent or multivalent cation-containing compound and the second divalent or multivalent cation-releasing compound being present in a predetermined concentration; wherein the $K_{sp}$ of the second cation-containing compound is greater than the $K_{sp}$ of the first cation-containing compound; wherein at least one of the monomers is selected from the group consisting of acids, monomers containing an acid group, monomers containing a derivative of an acid, and mixtures thereof, wherein the at least one monomer reacts with the first and second divalent or multivalent cations to form ionic cross-links inter-molecularly among polymer chains to form an ionically cross-liked hydrogel composition at a gelation rate; wherein the hydrogel composition contains a ratio of first divalent or multivalent cation-containing and divalent or multivalent cation-releasing compound to second divalent or multivalent cation-containing and divalent or multivalent cation-releasing compound; and wherein the first and second divalent or multivalent cations are selected from the group consisting of calcium, beryllium, strontium, barium, radium, aluminum, copper, zinc, osnium, and mixtures thereof;
wherein the controlling step is accomplished by varying at least one of: solubility of the first and second cation-containing compounds; cation concentration; the ratio; polymer concentration; and gelation temperature.

17. The method as defined in claim 16 wherein the polymer is selected from the group consisting of sodium alginate, potassium alginate, and mixtures thereof, the fast dissolving/releasing compound is calcium sulfate dihydrate ($CaSO_4.2H_2O$), the slow dissolving/releasing compound is calcium carbonate ($CaCO_3$), and wherein the composition further consists essentially of D-glucono-delta-lactone (GDL).

18. The method as defined in claim 17 wherein the calcium ion to carboxyl molar ratio ranges between about 0.05 and about 2.0, and wherein the ratio of $CaCO_3$ to $CaSO_4.2H_2O$ ranges between about 98:2 and about 2:98.

19. The method as defined in claim 18 wherein the calcium ion to carboxyl molar ratio ranges between about 0.27 and about 0.54, and wherein the ratio of $CaCO_3$ to $CaSO_4.2H_2O$ ranges between about 65:35 and about 85:15.

20. A hydrogel composition, comprising:
at least one water-soluble polymer composed of one or more monomers, the polymer being present in a predetermined concentration;
at least one of: a first cation-containing compound composed of calcium sulfate dihydrate ($CaSO_4.2H_2O$); and a first divalent or multivalent cation-releasing compound, the at least one first cation-containing compound and the first cation-releasing compound being present in a predetermined concentration; and
at least one of: a second cation-containing compound composed of calcium carbonate ($CaCO_3$); and a second divalent or multivalent cation-releasing compound, the at least one second cation-containing compound and the second cation-releasing compound being present in a predetermined concentration;
wherein at least one of the monomers is selected from the group consisting of acids, monomers containing an acid group, monomers containing a derivative of an acid, and mixtures thereof, wherein the at least one monomer reacts with the divalent or multivalent cations to form ionic cross-links inter-molecularly among polymer chains to form an ionically cross-linked hydrogel composition.

21. The hydrogel composition as defined in claim 20 wherein the polymer is selected from the group consisting of alginic acid, pectin, hyaluronic acid, heparin, proteins, proteoglycans, poly(methacrylic acid), poly(acrylic acid), poly(maleic anhydride), poly(maleic acid), poly(methyl methacrylate-methacrylic acid), poly(methyl acrylate-acrylic acid), poly(methyl methacrylate-acrylic acid), poly(ethyl acrylate-acrylic acid), poly(ethyl methacrylate-methacrylic acid), poly(butyl acrylate-acrylic acid), poly(ethylene-acrylic acid), poly(ethylene-methacrylic acid), poly(acrylo-nitrile-maleic anhydride), poly(butadiene-acrylonitrile-acrylic acid), poly(butadiene-maleic acid), poly(butadiene-maleic anhydride), poly(acrylamide-acrylic acid), poly(2-hydroxyethyl methacrylate-methacrylic acid), poly(propylene-acrylic acid), poly(propylene-ethylene-acrylic acid), poly(vinyl chloride-vinyl acetate-maleic acid), derivatives thereof, and mixtures thereof.

22. The hydrogel composition as defined in claim 20, wherein the hydrogel composition contains a predetermined ratio of the first cation-containing compound to the second cation-containing compound, wherein the predetermined ratio substantially controls the gelation rate.

23. The hydrogel composition as defined in claim 22 wherein a calcium ion to carboxyl molar ratio ranges between about 0.05 and about 2.0, and wherein the ratio of $CaCO_3$ to $CaSO_4.2H_2O$ ranges between about 98:2 and about 2:98.

24. The hydrogel composition as defined in claim 22 wherein a calcium ion to carboxyl molar ratio ranges between about 0.18 and about 0.90, and wherein the ratio of $CaCO_3$ to $CaSO_4.2H_2O$ ranges between about 98:2 and about 2:98.

25. The hydrogel composition as defined in claim 22 wherein a calcium ion to carboxyl molar ratio ranges between about 0.27 and about 0.54, and wherein the ratio of $CaCO_3$ to $CaSO_4.2H_2O$ ranges between about 65:35 and about 85:15.

26. A biocompatible hydrogel composition, consisting essentially of:
at least one water-soluble polymer formed by polymerization of one or more monomers, the polymer being present in a predetermined concentration;

at least one of: a first cation-containing compound composed of calcium sulfate dihydrate ($CaSO_4 \cdot 2H_2O$); and a first divalent or multivalent cation-releasing compound, the at least one first cation-containing compound and the first divalent or multivalent cation-releasing compound being present in a predetermined concentration; and at least one of: a second cation-containing compound composed of calcium carbonate ($CaCO_3$); and a second divalent or mutlivalent cation-releasing compound, the at least one second cation-containing compound and the second divalent or multivalent cation-releasing compound being present in a predetermined concentration;

wherein at least one of the monomers is selected from the group consisting of acids, monomers containing an acid group, monomers containing a derivative of an acid, and mixtures thereof, wherein the at least one monomer reacts with the divalent or mutlivalent cations to form ionic cross-links inter-molecularly among polymer chains to form an ionically cross-linked hydrogel composition at a gelation rate;

and wherein the hydrogel composition contains a predetermined ratio of calcium sulfate dihydrate ($CaSO_4 \cdot 2H_2O$) to calcium carbonate ($CaCO_3$), wherein the ratio of calcium sulfate dihydrate ($CaSO_4 \cdot 2H_2O$) to calcium carbonate ($CaCO_3$) substantially controls the gelation rate.

27. The biocompatible hydrogel composition as defined in claim 26 wherein the polymer is selected from the group consisting of sodium alginate, potassium alginate, and mixtures thereof, and wherein the composition further consists essentially of D-glucono-delta-lactone (GDL).

28. The biocompatible hydrogel composition as defined in claim 26 wherein a calcium ion to carboxyl molar ratio ranges between about 0.05 and about 2.0, and wherein the ratio of $CaCO_3$ to $CaSO_4 \cdot 2H_2O$ ranges between about 98:2 and about 2:98.

29. The biocompatible hydrogel composition as defined in claim 26 wherein a calcium ion to carboxyl molar ratio ranges between about 0.27 and about 0.54, and wherein the ratio of $CaCO_3$ to $CaSO_4 \cdot 2H_2O$ ranges between about 65:35 and about 85.15.

* * * * *